US00PP17869P2

(12) United States Plant Patent
Dittmar

(10) Patent No.: US PP17,869 P2
(45) Date of Patent: Jul. 17, 2007

(54) ***SANVITALIA* PLANT NAMED 'STARBINI'**

(50) Latin Name: *Sanvitalia speciosa*
Varietal Denomination: Starbini

(75) Inventor: Hugo Dittmar, Deitingen (CH)

(73) Assignee: InnovaPlant GmbH + Co. KG, Gensingen (DE)

( * ) Notice: Subject to any disclaimer, the term of this patent is extended or adjusted under 35 U.S.C. 154(b) by 0 days.

(21) Appl. No.: 11/299,957

(22) Filed: Dec. 12, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Sanvitalia* plant named 'Starbini', characterized by its compact, outwardly spreading and low-mounded plant habit; freely branching habit and short internodes, dense and bushy plants; dark green-colored foliage; long and freely flowering habit with flowers held just above and beyond the foliage; and single daisy inflorescence form with yellow-colored ray florets.

1 Drawing Sheet

Botanical designation: *Sanvitalia speciosa.*
Cultivar denomination: 'Starbini'.

BACKGROUND OF THE INVENTION

The present invention relates to a new and distinct cultivar of *Sanvitalia* plant, botanically known as *Sanvitalia speciosa* and hereinafter referred to by the cultivar name 'Starbini'.

The new *Sanvitalia* is a product of a planned breeding program conducted by the Inventor in Deitingen, Switzerland. The objective of the program is to create and develop new compact *Sanvitalia* cultivars with numerous inflorescences and attractive ray floret coloration.

The new *Sanvitalia* originated from a cross-pollination by the Inventor of two unnamed *Sanvitalia speciosa* seedling selections, not patented. The new *Sanvitalia* was discovered and selected by the Inventor as a plant within the progeny of the stated cross-pollination in a controlled environment in Deitingen, Switzerland in 2001. The selection of the new *Sanvitalia* was based on its compact and freely flowering habit.

Asexual reproduction of the new *Sanvitalia* by terminal cuttings in a controlled environment in Deitingen, Switzerland since 2001, has shown that the unique features of this new *Sanvitalia* are stable and reproduced true to type in successive generations.

SUMMARY OF THE INVENTION

The new *Sanvitalia* has not been observed under all possible environmental conditions. The phenotype may vary somewhat with variations in environment such as temperature and light intensity without, however, any variance in genotype.

The following characteristics have been repeatedly observed and are determined to be basic characteristics of 'Starbini' and distinguish the new *Sanvitalia* as a new and distinct cultivar:

1. Compact, outwardly spreading and low-mounded plant habit.
2. Freely branching habit and short internodes, dense and bushy plants.
3. Dark green-colored foliage.
4. Long and freely flowering habit with flowers held just above and beyond the foliage.
5. Single daisy inflorescence form with yellow-colored ray florets.

Plants of the new *Sanvitalia* differ from plants of the parent selections primarily in plant growth habit as plants of the new *Sanvitalia* are more uniform and more compact than plants of the parent selections.

Plants of the new *Sanvitalia* can be compared to plants of the cultivar Dittsun, disclosed in U.S. Plant Pat. No. 14,140. In side-by-side comparisons conducted in Deitingen, Switzerland, plants of the new *Sanvitalia* differed from plants of the cultivar Dittsun in the following characteristics:

1. Plants of the new *Sanvitalia* were more outwardly spreading than and not as upright as plants of the cultivar Dittsun.
2. Plants of the new *Sanvitalia* and the cultivar Dittsun differed in leaf coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Sanvitalia.*

The photograph at the bottom of the sheet comprises a side perspective view of a typical flowering plant of 'Starbini' grown in a container.

The photograph at the top of the sheet comprises a close-up view of typical leaves and inflorescences of 'Starbini'.

DETAILED BOTANICAL DESCRIPTION

The aforementioned photographs, following observations and averaged measurements describe plants grown in Bonsall, Calif., in a polyethylene-covered greenhouse during the fall with day temperatures ranging from 13° C. to 35° C. and night temperatures ranging from 4° C. to 13° C. Plants were grown for about 14 weeks in 15-cm containers. Color references are made to The Royal Horticultural Society Colour Chart, 1995 Edition, except where general terms of ordinary dictionary significance are used.

Botanical classification: *Sanvitalia speciosa* cultivar Starbini.

Parentage: Cross-pollination of two unnamed seedling selection of *Sanvitalia speciosa,* not patented.

Propagation:

*Type.*—Terminal vegetative cuttings.

*Time to initiate roots.*—Summer: About 14 days at 20° C. to 22° C. Winter: About 18 days at 20° C. to 22° C.

*Time to produce a rooted cutting.*—Summer: About 21 days at 18° C. to 20° C. Winter: About 25 days at 18° C. to 20° C.

*Root description.*—Fine; white in color.

Plant description:

*General appearance.*—Compact, outwardly spreading and low-mounding plant form with dense foliage and inflorescences held just above and beyond the foliage. Moderately vigorous growth habit. Freely branching habit with four primary lateral branches each with secondary lateral branches potentially developing at every node; dense and bushy plant habit.

*Plant height.*—About 15 cm.

*Plant width, per plant.*—About 40 cm.

*Lateral branch description.*—Length: About 26 cm. Diameter: About 3 mm. Internode length: About 2.5 cm to 3 cm. Aspect: Initially upright then falling outwardly. Texture: Slightly pubescent. Color: 148B tinged with 183A.

*Foliage description.*—Arrangement: Opposite, simple. Length: About 2.4 cm. Width: About 9 mm. Shape: Elliptic. Apex: Broadly acute. Base: Attenuate. Margin: Entire. Texture, upper and lower surfaces: Slightly pubescent and coarse. Venation pattern: Pinnate. Color: Developing and fully expanded foliage, upper surface: 147A; venation, 147B. Developing and fully expanded foliage, lower surface: 147B; venation, 147D. Petiole length: About 3 mm. Petiole diameter: About 2.5 mm. Petiole texture, upper and lower surfaces: Slightly pubescent. Petiole color, upper surface: 147D. Petiole color, lower surface: 147C.

Inflorescence description:

*Appearance.*—Single daisy composite inflorescence form with ligulate ray florets. Disc and ray florets arranged acropetally on a capitulum. Inflorescences held upright on terminal and axillary peduncles. Inflorescences upright to outward and perpendicular to the peduncles. Inflorescences persistent. Inflorescences not fragrant.

*Flowering response.*—Long flowering season; plants flower continuously from April to October in Southern California.

*Inflorescence longevity.*—Inflorescences last about seven to ten days on the plant.

*Quantity of inflorescences.*—Freely flowering, about 250 inflorescence buds and open inflorescences per plant.

*Inflorescence size.*—Diameter: About 1.7 cm. Depth (height): About 6 mm. Diameter of disc: About 6 mm. Receptacle diameter: About 1.3 cm. Receptacle height: About 3 mm.

*Inflorescence buds.*—Height: About 5 mm. Diameter: About 7 mm. Shape: Oblate. Color: 144A.

*Ray florets.*—Quantity per inflorescence: About 13 arranged in a single whorl. Shape: Ligulate to elliptic. Length: About 8 mm. Width: About 3 mm. Apex: Slightly emarginate. Base: Attenuate. Margin: Entire. Texture, upper and lower surfaces: Smooth, glabrous; satiny. Aspect: Initially upright; when mature, about 75° from vertical; apices recurved. Color: When opening and fully opened, upper surface: 13A. When opening and fully opened, lower surface: 144B to 144C.

*Disc florets.*—Arrangement: Massed at the center of the inflorescence. Quantity per inflorescence: About 88. Shape: Tubular, five-parted at apex; apex, acute; base, fused. Length: About 3 mm. Diameter, apex: About 1 mm. Diameter, base: Less than 1 mm. Color: Immature: 144A. Mature, apex: 146C. Mature, midsection: 148D. Mature, base: 150D.

*Involucral bracts* (*phyllaries*).—Quantity per inflorescence: About five arranged in a single whorl. Length: About 6 mm. Width: About 5 mm. Shape: Ovate to elliptic. Apex: Acute. Base: Truncate. Margin: Entire. Texture, upper and lower surfaces: Slightly pubescent. Color, upper and lower surfaces: 146A.

*Peduncle.*—Strength: Strong. Aspect: Upright to horizontal. Length: About 2 cm. Diameter: About 1 mm. Texture: Pubescent. Color: 148B tinged with 183A.

*Reproductive organs.*—Androecium: Present on disc florets only. Quantity per floret: Five. Anther shape: Oblong. Anther length: Less than 1 mm. Anther color: 145A. Amount of pollen: Scarce. Pollen color: 145A. Gynoecium: Quantity per floret: One. Pistil length: About 4 mm. Stigma shape: Rounded. Stigma color: 145B. Style length: About 2 mm. Style color: 145B to 145C. Ovary color: 144B. Seed/fruit: Seed and fruit production has not been observed.

Disease/pest resistance: Resistance to pathogens and pests common to *Sanvitalias* has not been observed on plants grown under commercial conditions.

Temperature/weather tolerance: Plants of the new *Sanvitalia* have been observed to be tolerant to rain, wind and to temperatures from 2° C. to 35° C.

It is claimed:

1. A new and distinct cultivar of *Sanvitalia* plant named 'Starbini', as illustrated and described.

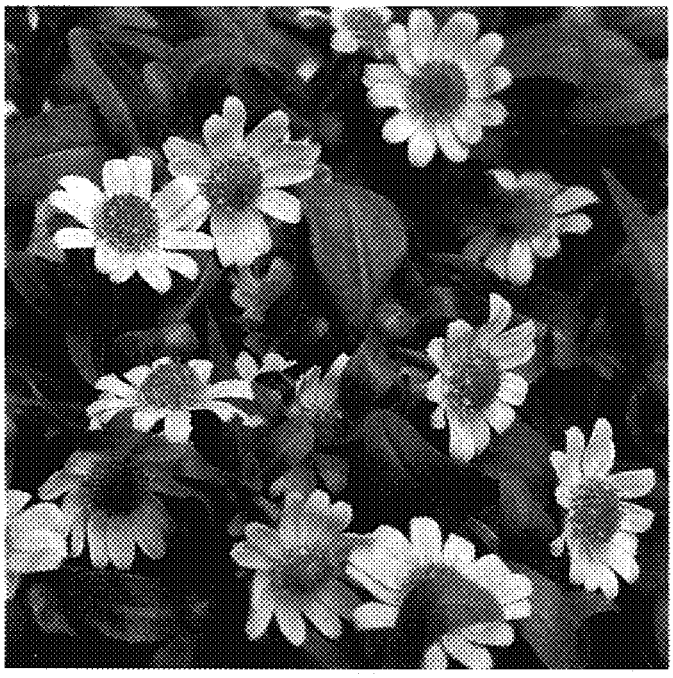
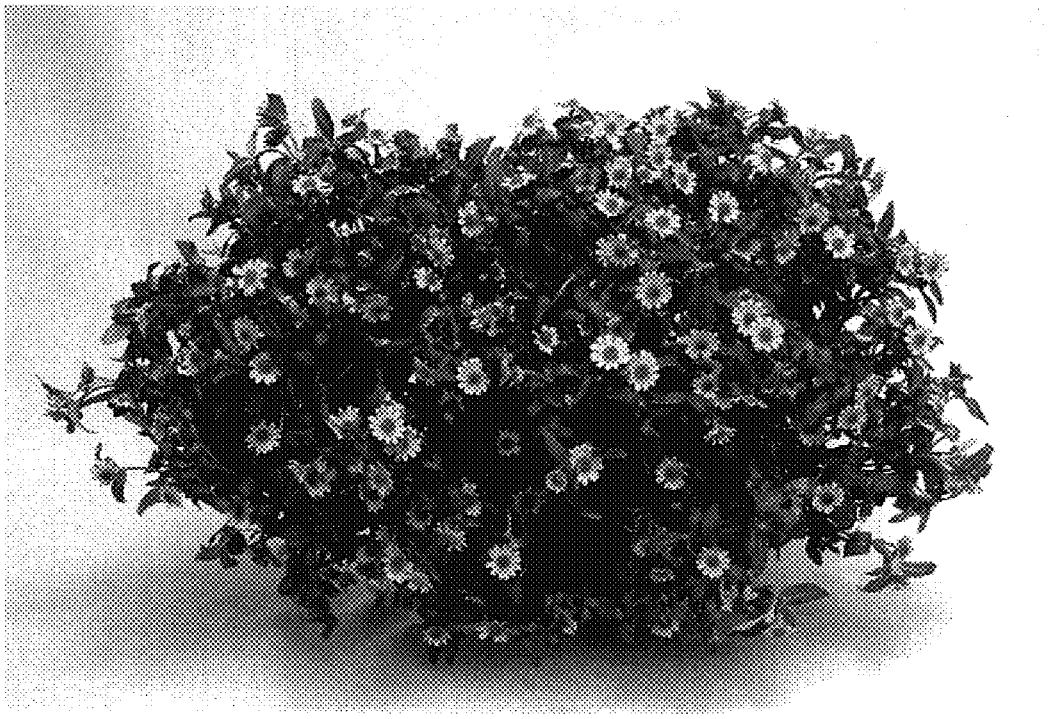

* * * * *